(12) United States Patent
Kajitani et al.

(10) Patent No.: US 6,660,043 B2
(45) Date of Patent: Dec. 9, 2003

(54) ARTIFICIAL HAND

(75) Inventors: Isamu Kajitani, Tsukuba (JP); Tetsuya Higuchi, Tsukuba (JP)

(73) Assignee: National Institute of Advanced Industrial Science and Technology, Tokyo (JP)

(*) Notice: Subject to any disclaimer, the term of this patent is extended or adjusted under 35 U.S.C. 154(b) by 0 days.

(21) Appl. No.: 10/157,160

(22) Filed: May 30, 2002

(65) Prior Publication Data

US 2003/0195638 A1 Oct. 16, 2003

(30) Foreign Application Priority Data

Apr. 16, 2002 (JP) .......................... 2002-112846

(51) Int. Cl.[7] .................................................. A61F 2/54
(52) U.S. Cl. ........................................ 623/64; 901/30
(58) Field of Search ....................... 623/61, 64; 901/29, 901/30, 31, 38, 39

(56) References Cited

U.S. PATENT DOCUMENTS

| | | | | |
|---|---|---|---|---|
| 4,149,278 A | * | 4/1979 | Wiker et al. ................. | 3/12.5 |
| 4,402,234 A | * | 9/1983 | Malarz et al. ................ | 74/417 |
| 5,888,246 A | * | 3/1999 | Gow ........................... | 623/64 |

FOREIGN PATENT DOCUMENTS

| | | | |
|---|---|---|---|
| JP | 55-99248 | * | 7/1980 |
| JP | 55099248 | | 7/1980 |
| JP | 10201782 | | 8/1998 |
| JP | 11056885 | | 3/1999 |
| JP | 2001104349 | | 4/2001 |
| WO | 99/21517 | * | 5/1999 |

\* cited by examiner

*Primary Examiner*—Bruce Snow
(74) *Attorney, Agent, or Firm*—Antonelli, Terry, Stout & Kraus, LLP

(57) ABSTRACT

An artificial hand is constructed to sufficiently rotate the fingers as a unit using a smaller small-sized motor by decreasing the magnitude of the radius of rotation of its rotating motion. The artificial hand has a support part for rotatably supporting the fingers; a conversion device for converting a rotating output of a driving device to a linear motion; and a finger opening-and-closing operation part for converting a linear motion of the conversion device to an opening-and-closing operation of the fingers. A holding part rotatably holds the support part above or at an upper part of the driving device; and another driving device is arranged in a terminal device held by a wrist part. A rotating output of another driving device is converted to a rotational motion of the support part; and a rotating mechanism rotates the fingers and driving device as a unit around the holding part.

20 Claims, 5 Drawing Sheets

ARTIFICIAL HAND

BACKGROUND OF THE INVENTION

1. Field of the Invention

The present invention relates to an electrically driven artificial hand which has a plurality of fingers capable of being opened and closed.

2. Prior Art

The artificial hand means an artificially formed hand which a person having a congenital defect in his upper limb or a postnatal defect in his upper limb due to an accident uses instead of the defected hand.

In Japanese Patent Application Laid-Open No.55-99248, there is disclosed an artificial hand which comprises a plurality of fingers opposite to one another; a grasp part having support members for rotatably supporting a base end part of each of the fingers; an electric artificial hand frame for holding the supporting member; a small-sized motor attached to the artificial hand frame; a reduction mechanism linked to the small-sized motor; a changing mechanism for changing rotating motion of the output part of the reduction mechanism to linear reciprocal motion; and a link mechanism for opening and closing the finger by the linear reciprocal motion of the output part of the changing mechanism.

Further, in Japanese Patent Application Laid-Open No.11-56885, there is disclosed an electric artificial hand which comprises a plurality of fingers opposite to one another; a grasp part having support members for rotatably supporting a base end part of each of the fingers; a solenoid actuator for reciprocally moving its output part; and a link mechanism for opening and closing each of the fingers of the holding part by linking the reciprocal motion of the output part.

A thumb form variable type artificial hand is disclosed in Japanese Patent Application laid-Open No.2201-104349, and a control unit for a electric artificial hand is disclosed in Japanese Patent Application Laid-Open No.10-201782.

As described above, it has been known that the fingers are opened and closed using the link mechanism by changing the rotating motion of the small-sized motor to the linear motion. The finger is supported by the supporting member, and the supporting member is held by the grasp part or a terminal device linked to the hand part, and the terminal device has a rotation hub for changing the direction of the terminal device, that is, the fingertips is arranged at a position corresponding to the human wrist, that is, at a position of a linking part between the wrist part and the terminal device. Accordingly, all of the terminal device and the fingers arranged in front of the wrist must be rotated at the position corresponding to the wrist described above, which requires a little larger motor though it is a small-sized motor.

SUMMARY OF THE INVENTION

An object of the present invention is to provide an artificial hand which can sufficiently rotate the whole fingers using a smaller small-sized motor by decreasing the magnitude of the radius of rotation of its rotating motion.

In the present invention, the above-mentioned problem is solved by rotating the terminal device at a position corresponding to the root portion of the fingers.

In the concrete, the present invention provides an artificial hand comprising a plurality of fingers opposite to one another; a support part for rotatably supporting the fingers; a driving device mounted on a grasp part integrated with the support part; and a finger opening-and-closing operation part for converting a rotation output of the driving device to an opening-and-closing operation of the fingers (which may be replaced by a conversion device for converting a rotating output of the driving device to a linear motion, and the linear motion of the conversion device is converted to an opening-and-closing operation), which further comprises a hold part for rotatably holding the support part arranged above or at an upper part of the driving device; a terminal device held by a wrist part; another driving device arranged in the terminal device, a rotating output of the another driving device being converted to a rotational motion of the support part; and a rotating mechanism for rotating the fingers and the driving device around the hold part.

Further, the present invention provides an artificial hand in which the rotating mechanism is constructed of a worm gear rotated by the another driving device; and a rotation gear for rotating the terminal device, the rotation gear being driven by engaging with the worm gear.

Further, the present invention provides an artificial hand in which the rotation gear has a stopper for limiting a rotation angle.

DESCRIPTION OF THE PREFERRED EMBODIMENTS

Embodiment of the present invention will be described below, referring to the accompanied figures.

Figure 1:
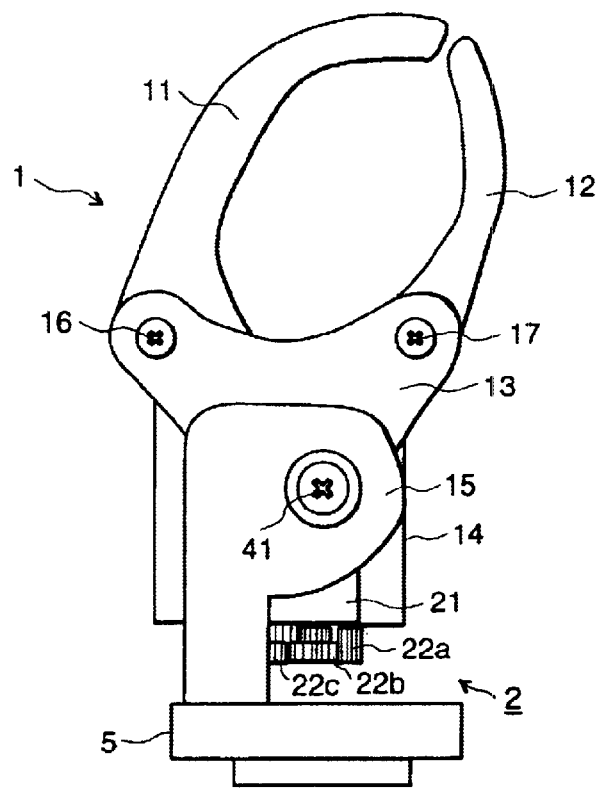
FIG. 1 is a schematic view showing the total construction of an embodiment of an artificial hand in accordance with the present invention.

FIG. 1 is a schematic view showing the total construction of an embodiment of an artificial hand in accordance with the present invention. Referring to FIG. 1, the artificial hand 100 comprises fingers 11 (a first finger) and 12 (a second finger) opposite to one another; a support body (member) 13 for supporting the fingers 11 and 12; a grasp part 14 integrated with the support part (body) 13; and a terminal device 15 held by a wrist part 5.

The fingers 11 and 12 are rotatably supported to the support part 13 by pivots 16 and 17. The terminal device 15 has a holding part 41 to rotatably hold the support part 13. The support part 13 can be also made rotatable by holding the grasp part 14 by the hold part 41.

A micromotor 21 of a drive device is arranged in the grasp part 14, and a reduction device 2 composed of a group of gears is provided to a driving shaft of the motor 21. The group of gears has a reduction gear 1 (22a) rotated by the rotation output of the motor 21; a reduction gear 2 (22b) rotated by the reduction gear 1; and a reduction gear 3 (22c).

An ultrasonic motor for slewing motion and a group of planet gears for reducing rotation speed of the ultrasonic motor, not shown in the figure, are provided in the terminal device 5 so that the whole artificial hand 100 may be slewed. A well-known construction may be employed for this construction. The key point is that the planet gear is rotated by the slewing ultrasonic motor to slew the terminal device 15 by the rotation of the planet gear.

Figure 2:
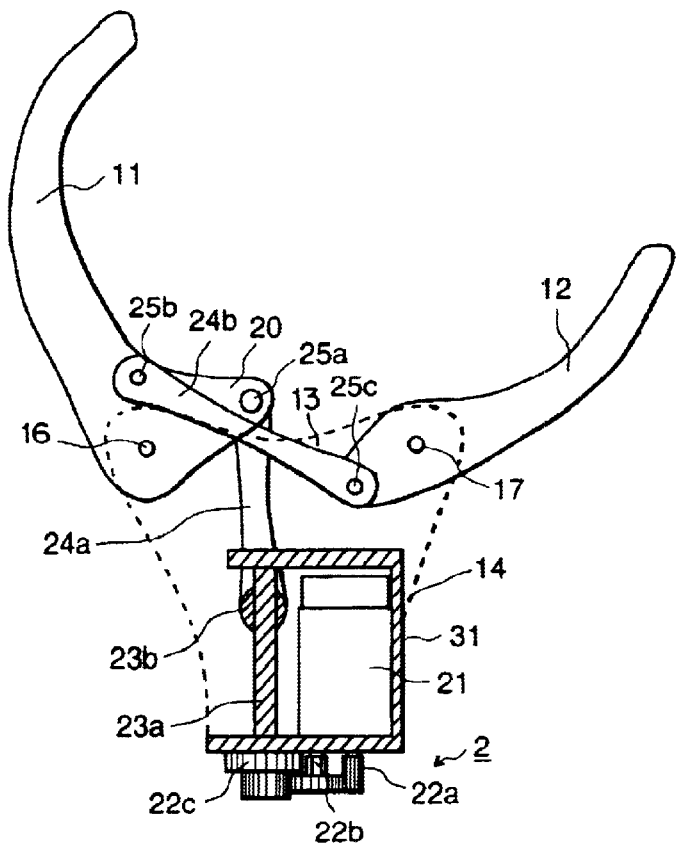
FIG. 2 is a view showing a part of the construction of FIG. 1.

FIG. 2 shows the finger opening-and-closing mechanism 1 for performing opening-and-closing operation of the fingers 11 and 12 using a link mechanism in the construction of FIG. 1.

The finger opening-and-closing mechanism 1 comprises the motor 21 held on the grasp part 14 (in the figure, drawn as a one-piece structure together with the support part 13) by a hold device 31; the reduction device 2 composed of the group of gears arranged the outer bottom part of the hold device 31; a feed screw 23a of a rod screw held by a shaft, not shown, inside the hold device 31; a nut part 23b; a link 1 (24a); and a link 2 (24b). Therein, the hold device 31 and the grasp part 14 may be integrated into a one-piece structure to form a grasp part 14. As shown in the figure, the link 2 (24b) is rotatably linked to the fingers 11 and 12 in an upper portion of a pivot 16 in regard to the finger 11 and in a lower portion of a pivot 17 in regard to the finger 12 using pivots 25b and 25c, respectively. Further, the link 24a is rotatably linked to the finger 11 by a pivot 25a provided in an upward projecting part 20 of the finger 11.

Figure 3:
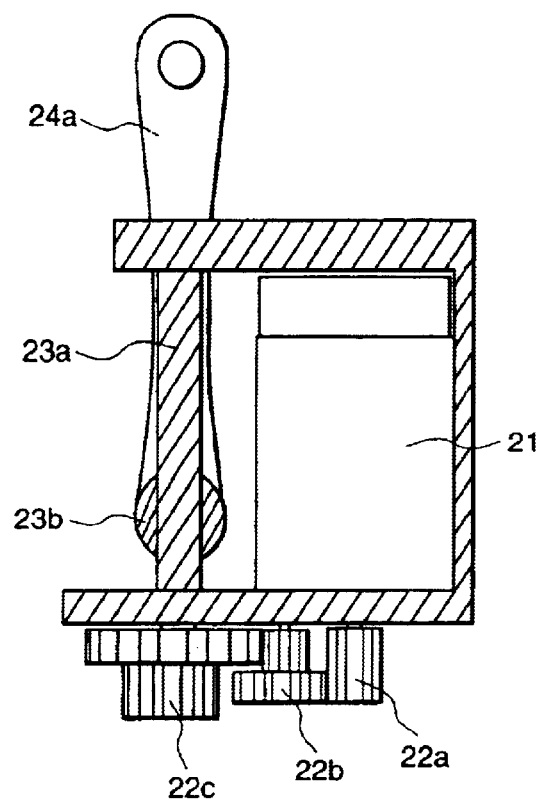
FIG. 3 is a vertical detailed view showing a part of the construction of FIG. 2.
Figure 4:
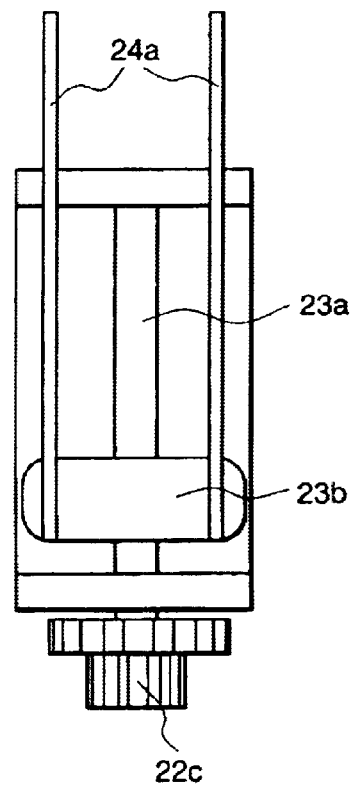
FIG. 4 is a side view showing the construction of FIG. 3.

Referring to FIG. 3 and FIG. 4, the motor 21 is the finger opening-and-closing motor which rotates the reduction gears 22a, 22b and 22c to rotate the feed screw 23a connected to the reduction gear 22c, and the nut part 23b is moved upward and downward by the rotation of the feed screw 23a to linearly move the link 1 (24a) of a slider integrated together with the nut part 23b. Thus, the fingers 11 and 12 are opened and closed by the link action by the linear motion of the link 24a. For example, when the link 1 (24a) is moved upward, the pivot 25a of the connection part is pushed upward to rotate the finger 11 anticlockwise around the pivot 16 and thus to open the fingertips. On the other hand, when the link 1 (24a) is moved downward, the pivot 25a is pulled downward to rotate the finger 11 clockwise around the pivot 16 and thus to close the fingertips.

When the fingertip of the finger 11 is opened, the finger 12 is rotated clockwise around the pivot 17 to open the fingertips because the-finger 11 and the finger 12 are linked each other by the link-2 (24b) and accordingly the pivot 25c is pulled by the link 2 (24b). On the other hand, when the fingertip of the finger 11 is closed, the finger 12 is rotated anticlockwise around the pivot 17 to close the fingertips because the pivot 25c is pushed in by the link 2 (24b).

Although in this example the rotation output is converted to the linear motion and then converted to the opening-and-closing operation of the fingers, the rotation output may be directly converted to the opening-and-closing operation depending on the combination of the gears.

Figure 5:
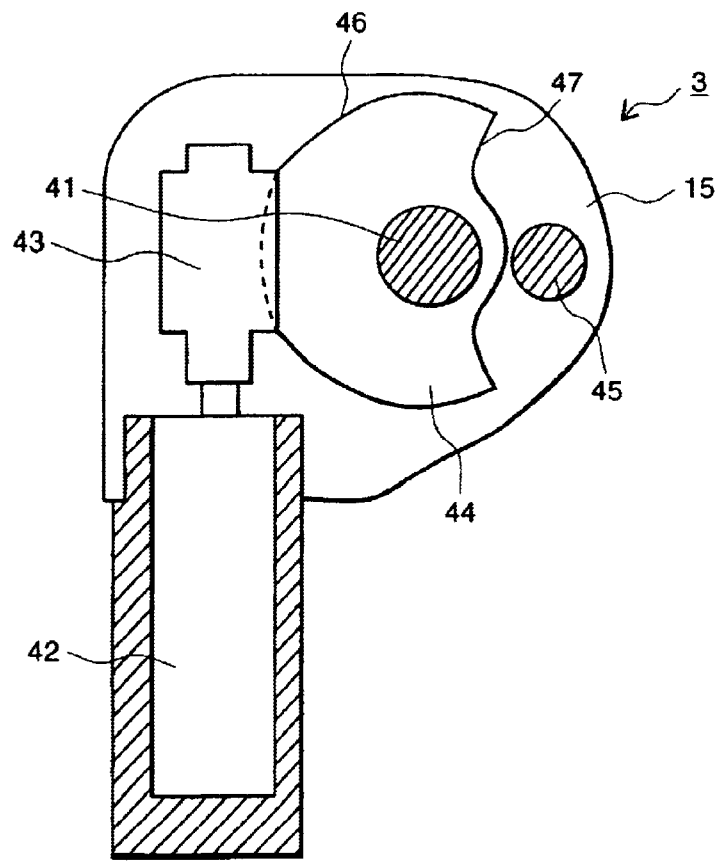
FIG. 5 is a view showing a part of the construction of FIG. 1.

FIG. 5 shows a rotating mechanism of the finger and the motor 21. The rotating mechanism 3 comprises the terminal device 15 connected to the grasp part 14 (FIG. 1) by the hold part 41 (a rotation shaft); a motor 42 of a second driving device provided in the terminal device 14; a worm gear 43 rotated by the motor 42; a rotation gear 44 engaging with the worm gear 43; and a stopper 45.

The worm gear 43 is rotated by the rotation output of the motor 42, and the rotation gear 44 is rotated around the hold part 41 by the rotation of the worm gear.

Since the rotation gear 44 is fixed to the grasp part 14 by the hold part 41, the grasp part 14 is slewed around the hold part 41 as the rotation gear 44 is rotated. The direction of the grasp part 14 is changed by the slewing, and the support part 13 and the fingers 11 and 12 are slewed together as the grasp part 14 is slewed to change the fingertip opening-and-closing direction. In this case, an important point is that the position of the hold part 41 is positioned above the motor 42. Although the hold part 41 can be positioned above the motor 42 by placing the other gears, it is preferable that the hold part 41 is located above the motor 42 because it means that the hold part can be placed near the root portion of the fingers 11 and 12.

By placing the hold part 41 above or the upper portion of the motor 42, the radius of rotation of the fingers 11 and 12 can be made smaller. In this case, the fingers 11, 12 and the motor 42 are vertically slewed around the hold part 41.

The outer periphery of the rotation gear 44 is constructed of a gear part 43 engaging with the worm gear 43 and a notch part 47. The stopper 45 is arranged in the notched portion. By doing so, the slewing of the rotation gear 44 is limited, and accordingly the slewing of the fingers 11 and 12 is limited.

Rotation of the rotation gear 44 is stopped at 45 degrees (a first angle) in the clockwise direction and at 30 degrees (a second angle) in the anticlockwise direction by the stopper 45. It is preferable to set the first angle larger than the second angle. As the result, the opening-and-closing direction of the grasp part 14 can be changed 45 degrees in the side of the finger 11 and 30 degrees in the side of the finger 12. In the above description, the rotation of the grasp part 14 and the fingers 11 and 12 as a whole is called as rotation, but it may be called as "bending and stretching" when the rotation range is restrictively used. In this case, the motor 42 is a bending-and-stretching motor, the worm gear 43 is rotated by the rotation of the motor 42, and the rotation gear, that is, the bending-and-stretching gear 44 is slewed by the rotation of the worm gear 43, and the fingers 11 and 12 are bent and stretched around the hold part 41 of the bending-and-stretching shaft.

Figure 6:
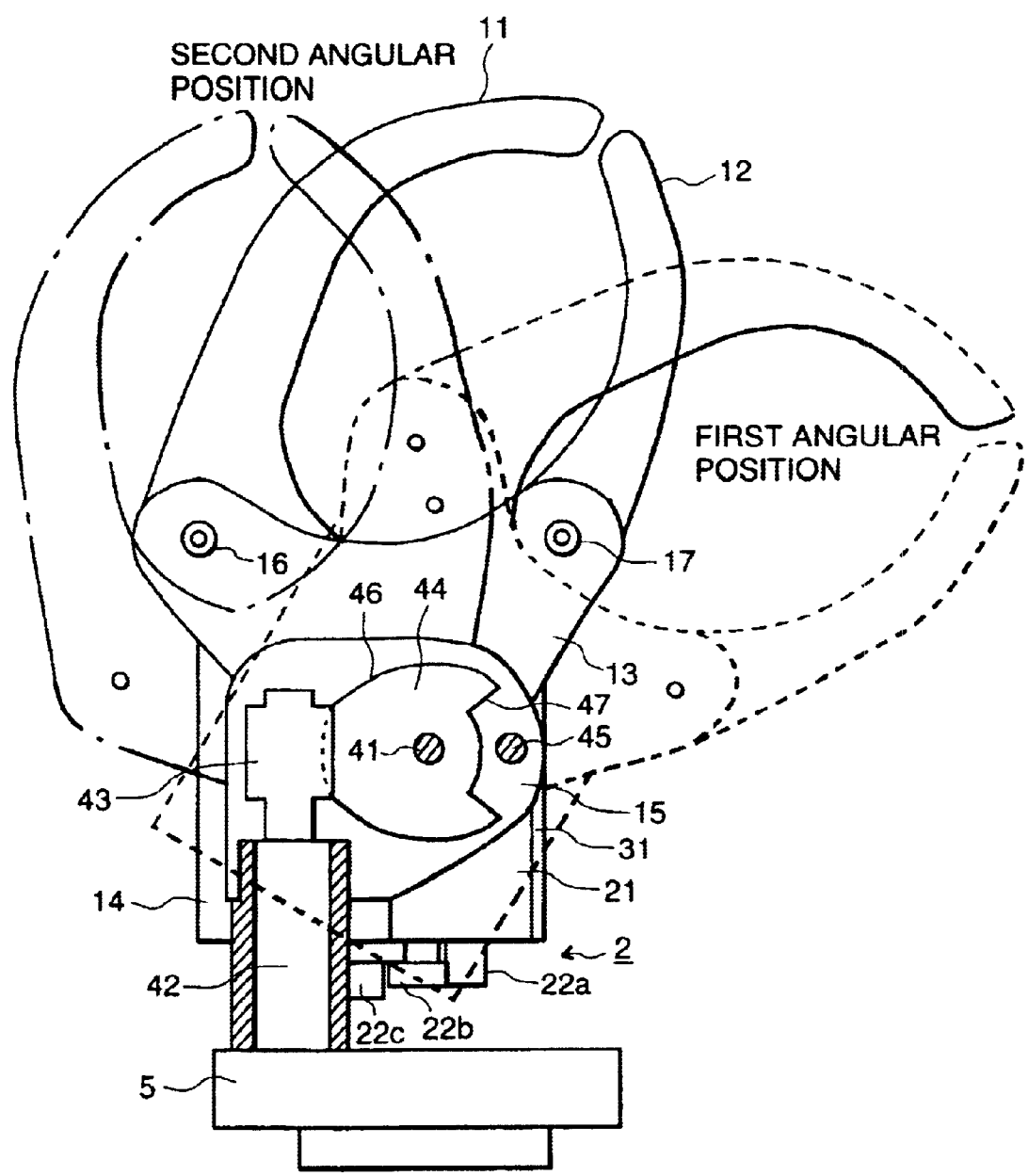
FIG. 6 is a view showing the integrated construction of FIG. 1 and FIG. 5.

The above-mentioned slewing, that is, the status of bending-and-stretching will be described below, referring to FIG. 6. FIG. 6 shows the integrated state of the structure shown in FIG. 2 and the structure shown in FIG. 5. Referring to the figure, the motor 21 is fixed to the hold device 31 or the grasp part 14, and the motor 42 is fixed to the terminal device 15 in parallel to the motor 21, and accordingly the output directions of both the motors are vertical and the same.

Now, it is assumed that the fingers 11 and 12 are in the position shown by the solid line. In this status, when the motor 42 is operated to rotate the rotation gear 44 by rotation of the worm gear 43, the grasp part 14 (the hold device 31) is slewed around the hold part 41 to be brought at a position shown by the dotted line when the grasp part 41 is slewed clockwise. By doing so, the fingers 11 and 12 are slewed (bent and stretched) together up to the first angler position shown by the dotted line. When the grasp part 41 is slewed anticlockwise, the fingers 11 and 12 are slewed together up to the second angler position shown by the chain line.

Figure 7:
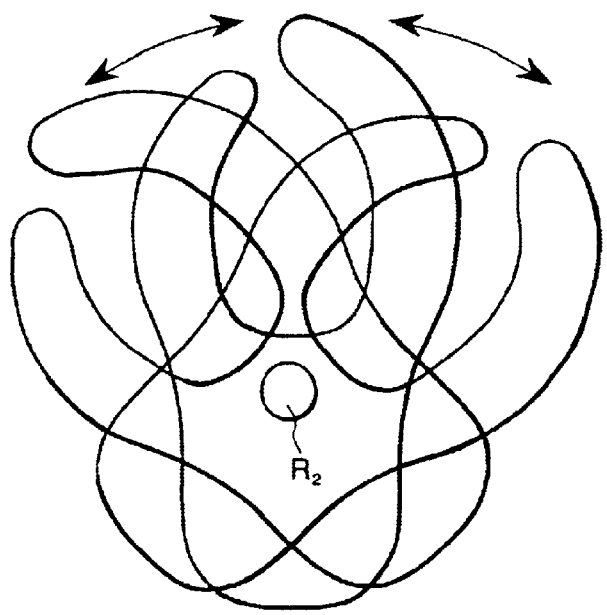
FIG. 7 is a view showing the feature of the present invention.

Comparison of slewing statuses will be made between a conventional example shown in FIG. 8 and the present embodiment shown in FIG. 7.

Figure 8:
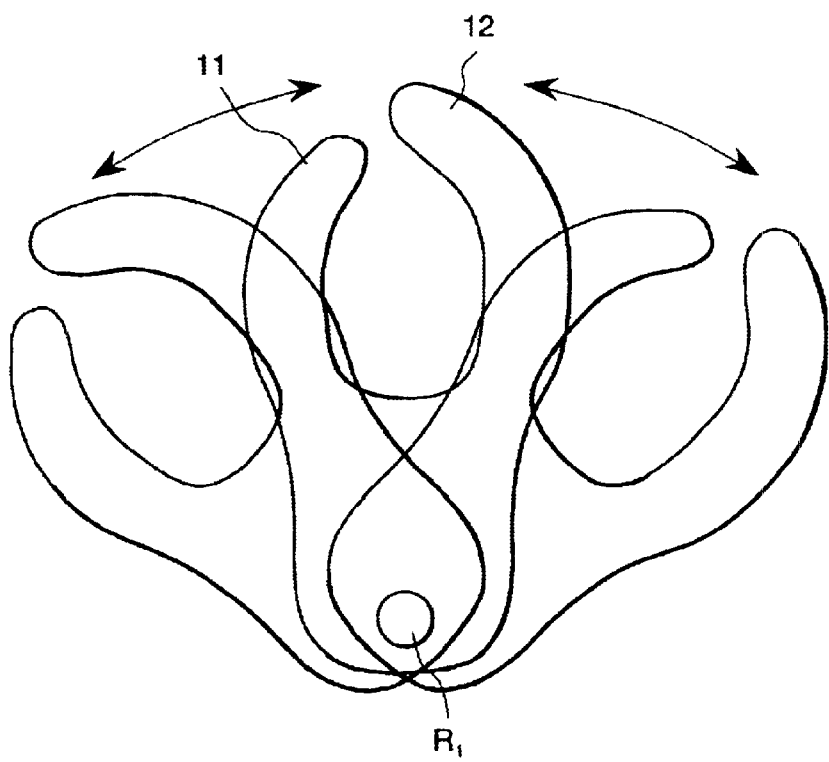
FIG. 8 is a view showing a function of a conventional artificial hand.

As shown in FIG. 8, according to the conventional method, the rotation center $R_1$ for changing the direction of the fingers 11 and 12 as a whole is in the position corresponding to the human wrist. Therefore, a larger motor is required in order to rotate the whole body in front of the wrist. On the other hand, according to the present embodiment, the fingers 11 and 12 and the grasp part 14 and so on can be rotated around the rotation center $R_2$ which is arranged in the root portion of the fingers. By doing so, the fingers 11 and 12 and the grasp part 14 and so on can be rotated by a smaller motor, and accordingly the artificial hand itself can be made smaller in size.

In regard to the artificial hand having a front limb of multi-degrees of freedom capable of changing the opening-and-closing direction, the total length of the conventional artificial hand is about 23 cm in minimum length. On the other hand, according to the present embodiment, the length can be shortened to about 17 cm. This length is nearly equal to the length of the commercial artificial hand having a front limb of a single degree of freedom, and accordingly the artificial hand having a front limb of multi-degrees of freedom: according to the present embodiment can be applied to almost all of the front limb mutilators including wrist dieresis.

In the past, the direction of the fingers has to be changed by largely moving the whole arm, for example, in order to hold a remote control device in a table. However, according to the present embodiment, the remote control device can be grasped by small bending and stretching of the artificial hand.

Figure 9:
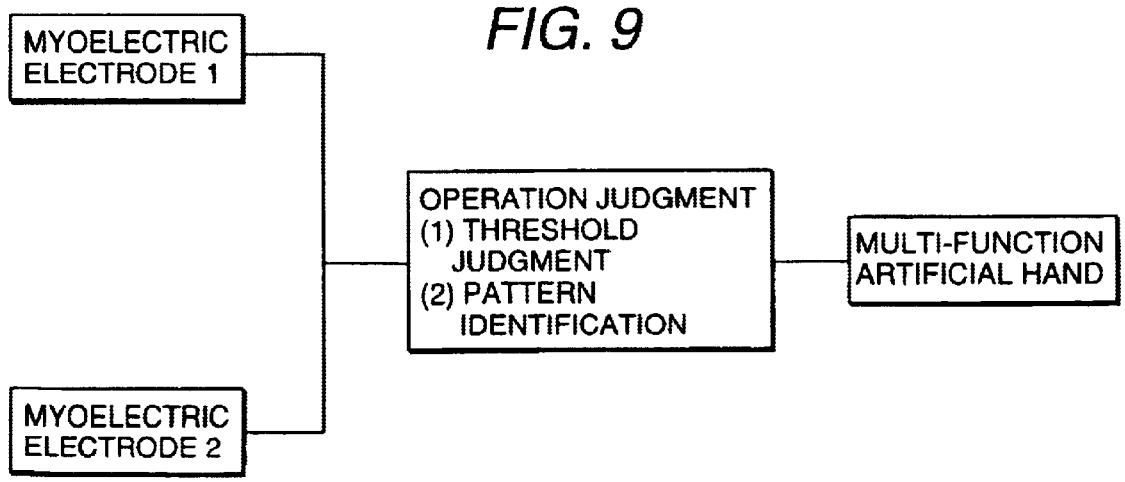
FIG. 9 is a block diagram showing the procedure of controlling the artificial hand in accordance with the present invention.

FIG. 9 shows the control method. In the figure, the myoelectric potential means an action potential which is generated when a muscle is constricted, and can be easily measured using an electrode in contact with a skin surface. The myoelectric artificial hand means an artificial hand capable of being operated by a myoelectric potential. A myoelectric potential generated from a muscle remaining in a cut end portion is generally used. However, if it is impossible, a myoelectric potential measured in the back or the like is sometimes used. The myoelectric artificial hand is also called as a myoelectric operating type artificial hand or a myoelectric motor-operated artificial hand. The control procedure will be described below.

Procedure 1

Two channels of myoelectric signals are measured using myoelectric electrodes in: contact with the skin surface of a cut end portion of a front limb or the other portion.

Procedure 2

It is judged from the measured two channels of the myoelectric signals which operation is intended to move the muscle, and an operation of the artificial hand is determined from the judged result.

Procedure 3

For the judgment, (A) threshold judgment and (B) pattern identification are used. (A) threshold judgment: When an intensity of the measured myoelectric potential exceeds a preset threshold, a corresponding operation is selected.

For Example, when an intensity of myoelectric potential signal measured in the bent muscle side exceeds a threshold value, the fingertips are closed. When an intensity of myoelectric potential signal measured in the stretched muscle side exceeds a threshold value, the fingertips are opened. (B) pattern identification: A combination pattern of the measured two channels of myoelectric potentials is discriminated using a pattern identifier such as a neural net work or a logic circuit to determine an operation of the artificial hand.

Procedure 4

Based on the judged results, the multi-function artificial hand is operated.

According to the embodiment described above, it is possible to construct an artificial hand comprising a plurality of fingers opposite to one another; a support part for rotatably supporting the fingers; driving devices mounted on a grasp part integrated with the support part; a conversion device for converting a rotating output of the driving device to a linear motion; and a finger opening-and-closing operation part for converting the linear motion of the conversion device to an opening-and-closing operation of the fingers, wherein two of the driving devices are arranged in parallel, one of the driving devices being rotatable together with the fingers, the other of the driving devices being rotatably arranged in a wrist part, one of the driving devices and the fingers being rotated together around a position near a root part of the fingers as the rotation center using the other of the driving devices. Further, it can be understood that the two driving devices are arranged at positions nearer to the fingers 11 and 12 than the slewing ultrasonic motor for the wrist part 5.

According to the present invention, it is possible is to provide an artificial hand which can sufficiently rotate the whole fingers using a smaller small-sized motor by decreasing the magnitude of the radius of rotation of its rotating motion, that is, the radius of rotation of its bending-and-stretching, and it is also possible to make the artificial hand itself smaller in size.

What is claimed is:

1. An artificial hand comprising a plurality of fingers disposed opposite to one another; a support body for rotatably supporting the fingers; a first driving device mounted on a grasping part integrated with said support body, said first driving device having an upper part and a lower part, the upper part being closer to said fingers than the lower part; and a finger opening-and-closing operation part for converting a rotation output of said driving device to an opening-and-closing operation of said fingers, which further comprises:

a holding part for rotatably holding said support body arranged above or at the upper part of said first driving device;

a terminal device held by a wrist part;

a second driving device arranged in said terminal device, a rotating output of said second driving device being converted to a rotational motion of said supports body; and a rotating mechanism for rotating said fingers and said first driving device as a unit around a longitudinal axis of said holding part and limiting rotating of said fingers and said first driving device around the longitudinal axis of said holding part between a first angular position and a second angular position.

2. An artificial hand according to claim 1, wherein said rotating mechanism is constructed of a worm gear rotated by said second driving device; and a rotation gear for rotating said holding part, said rotation gear being driven by engaging with said worm gear.

3. An artificial hand according to claim 2, wherein said rotation gear has a stopper for limiting rotation thereof.

4. An artificial hand according to claim 1, wherein said holding part is a rotation shaft.

5. An artificial hand according to claim 4, wherein each of said plurality of fingers is rotatably supported on said supporting body by a pivot.

6. An artificial hand according to claim 5, wherein a longitudinal axis of said pivot is parallel to the longitudinal axis of said holding part.

7. An artificial hand according to claim 1, wherein said holding part is arranged near a root part of said plurality of fingers.

8. An artificial hand according to claim 1, wherein rotation of said fingers and said first driving device as a unit around the longitudinal axis of said holding part rotates said plurality of fingers from an unrotated position clockwise to said first angular position and counter-clockwise to said second angular position.

9. An artificial hand according to claim 8, wherein an angular distance between the uncoated position and one of said first and second angular positions is larger than an angular distance between the unrotated position and the other of said first and second angular positions.

10. An artificial hand according to claim 9, wherein said first angular position is about 45 degrees in the clockwise direction from said unrotated position and said second angular position is about 30 degrees in the counter-clockwise direction from said unrotated position.

11. An artificial hand according to claim 9, wherein said holding part is a rotation shaft.

12. An artificial hand according to claim 8, wherein said holding part is a rotation shaft.

13. An artificial hand according to claim 12, wherein each of said plurality of fingers is rotatably supported on said supporting body by a pivot.

14. An artificial hand according to claim 13, wherein a longitudinal axis of said pivot is parallel to the longitudinal axis of said holding part.

15. An artificial hand according to claim 8, wherein said holding part is arranged near a root part of said plurality of fingers.

16. An artificial hand comprising a plurality of fingers disposed opposite to one another; a support body for rotatably supporting the fingers; a plurality of driving devices, at least one of which is mounted on a grasping part integrated with said support body; and a finger opening-and-closing operation part for converting a rotation output of one of said driving devices to an opening-and-closing operation of said fingers, wherein said one of said plurality of driving devices being mounted for rotation together with said fingers, and another of said plurality of driving devices being rotatably arranged in a wrist part, said one of said plurality of driving devices and the fingers being rotated together around a position near a root part of the fingers as the rotation center thereof using said another of said plurality of driving devices the rotation of said one of said plurality of driving devices and said fingers being limited between a first angular position and a second angular position.

17. An artificial hand comprising a plurality of fingers disposed opposite to one another; a support body for rotatably supporting the fingers; a first driving device mounted on a grasp part integrated with said support body, said first driving device having an upper part and a lower part, the upper part being closer to said fingers than the lower part; a conversion device for converting a rotating output of said first driving device to a linear motion; and a finger opening-and-closing operation part for converting the linear motion of said conversion device to an opening-and-closing operation of said fingers, which further comprises:

a holding part for rotatably holding said support body at a point above or at the upper part of said first driving device;

a terminal device held by a wrist part;

a second driving device arranged in said terminal device, a rotating output of said second driving device being converted to a rotational motion of said support body; and a rotating mechanism for rotating said fingers and said first driving device as a unit around a longitudinal axis of said holding part and limiting rotation of said fingers and said first driving device around the longitudinal axis of said holding part between a first angular position and a second angular position.

18. An artificial hand according to claim 17, wherein said rotating mechanism is constructed of a worm gear rotated by said second driving device, and a rotation gear for rotating said holding part, said rotation gear being driven by engaging with said worm gear.

19. An artificial hand according to claim 18, wherein said rotation gear has a stopper for limiting rotation thereof.

20. An artificial hand comprising a plurality of fingers disposed opposite to one another; a support body for rotatably supporting the fingers; a plurality of driving devices, at least one of which is mounted on a grasping part integrated with said support body; a conversion device for converting a rotating output of one of said driving devices to a linear motion; and a finger opening-and-closing operation part for converting the linear motion of said conversion device to an opening-and-closing operation of said fingers, wherein said one of said plurality of driving devices being mounted for rotation together with said fingers, and another of said plurality of driving devices being rotatably arranged in a wrist part, said one of said plurality driving devices and the fingers being rotated together around a position near a root part of the fingers as the rotation center thereof using said another of said plurality of driving devices, the rotation of said one of said plurality of driving devices and said fingers being limited between a first angular position and a second angular position.

* * * * *